United States Patent
Vandeputte et al.

(10) Patent No.: US 12,339,224 B2
(45) Date of Patent: Jun. 24, 2025

(54) METHOD AND APPARATUS FOR DETERMINATION OF TEXTILE FIBER COMPOSITION

(71) Applicant: VALVAN NV, Menen (BE)

(72) Inventors: Frank Vandeputte, Kortrijk (BE); Maurits Vandeputte, Ghent (BE); Peter Vandeputte, Wevelgem (BE)

(73) Assignee: VALVAN NV, Menen (BE)

( * ) Notice: Subject to any disclaimer, the term of this patent is extended or adjusted under 35 U.S.C. 154(b) by 381 days.

(21) Appl. No.: 17/612,085

(22) PCT Filed: May 22, 2020

(86) PCT No.: PCT/EP2020/064312
§ 371 (c)(1),
(2) Date: Nov. 17, 2021

(87) PCT Pub. No.: WO2020/234466
PCT Pub. Date: Nov. 26, 2020

(65) Prior Publication Data
US 2022/0214273 A1 Jul. 7, 2022

(30) Foreign Application Priority Data
May 23, 2019 (BE) .................................. 2019/5338

(51) Int. Cl.
*G01N 21/359* (2014.01)
*G01N 21/3563* (2014.01)
(Continued)

(52) U.S. Cl.
CPC ....... *G01N 21/359* (2013.01); *G01N 21/3563* (2013.01); *G01N 21/8851* (2013.01);
(Continued)

(58) Field of Classification Search
CPC .. G01N 21/259; G01N 21/31; G01N 21/8851; G01N 21/898; G01N 21/8983; G01N 2201/1296
See application file for complete search history.

(56) References Cited

U.S. PATENT DOCUMENTS 8,190,551 B2 5/2012 Busch
2019/0217342 A1* 7/2019 Parr ......................... B07B 1/14

FOREIGN PATENT DOCUMENTS

AT 504893 A4 9/2008
CN 107219188 A 9/2017
(Continued)

OTHER PUBLICATIONS

L. Liu, L. Yan, Y. Xie and G. Xia, "Content measurement of textile mixture by near infrared spectroscopy based on BP neural network," 2010 3rd International Congress on Image and Signal Processing, Yantai, China, 2010, pp. 3354-3358, doi: 10.1109/CISP.2010.5647632. (Year: 2010).*
Thermo Fisher Scientific, Thermo Scientific Antaris II Near-IR Analyzers, 2011 (Year: 2011).*
Liu, Li, et al. "Determination of fiber contents in blended textiles by NIR combined with BP neural network." International Scholarly Research Notices 2013 (2013). (Year: 2013).*
(Continued)

*Primary Examiner* — Catherine T. Rastovski
*Assistant Examiner* — Brian Butler Geiss
(74) *Attorney, Agent, or Firm* — Vorys, Sater, Seymour and Pease LLP

(57) ABSTRACT

The current invention concerns determining a fiber composition of a textile sample. The sample is irradiated with near infrared (NIR) light. Reflected NIR light from the sample is captured. A vector of spectral values is determined based on the captured light. The vector is input to a deep neural network (DNN). The DNN comprises a sequence of layers of nodes, in particular an input layer, at least two intermediate layers, and an output layer. The nodes of successive layers of the sequence are interconnected via weighted (Continued)

edges. The DNN outputs for each of a plurality of fiber material types a numerical relative composition amount.

20 Claims, 8 Drawing Sheets

(51) Int. Cl.
G01N 21/88 (2006.01)
G01N 21/898 (2006.01)
G01N 33/36 (2006.01)

(52) U.S. Cl.
CPC ....... *G01N 21/8983* (2013.01); *G01N 33/367* (2013.01); *G01N 2021/8883* (2013.01); *G01N 2201/0636* (2013.01); *G01N 2201/1296* (2013.01)

(56) References Cited

FOREIGN PATENT DOCUMENTS

| DE | 19920592 A1 | 11/2000 |
|----|-------------|---------|
| WO | 2004053220 A1 | 6/2004 |
| WO | 2020234466 A1 | 11/2020 |

OTHER PUBLICATIONS

Earl, Bill, Calibrating sensors. (May 18, 2015). Adafruit Learning System. https://learn.adafruit.com/calibrating-sensors/two-point-calibration (Year: 2015).*

Thermo Fisher Scientific, Advantages of a Fourier Transform Infrared Spectrometer, 2015 (Year: 2015).*

Xiting Sun, Hongfu Yuan, Chunfeng Song, Xiaoyu Li, Aiqin Hu, Shanshan Yu, Zhenxin Ren, A novel drying-free identification method of cashmere textiles by NIR spectroscopy combined with an adaptive representation learning classification method, Microchemical Journal, vol. 149, 2019 (Year: 2019).*

Zitting, J. Optical sorting technology for textile waste: Development of an identification method with NIR spectroscopy, 2017 (Year: 2017).*

Gabriele Mirschel, Olesya Daikos, Tom Scherzer, Carsten Steckert, Near-infrared chemical imaging used for in-line analysis of functional finishes on textiles, Talanta, vol. 188, 2018, pp. 91-98, ISSN 0039-9140) (Year: 2018).*

Chauhan, Neha, Nirmal Yadav, and Nisha Arya. "Applications of artificial neural network in textiles." International Journal current microbiol applied sciences 7 (2018): 3134-3143. (Year: 2018).*

ISR-WO dated Sep. 21, 2020 for PCT/EP2020/064312.

IPRP dated Jun. 22, 2021 for PCT/EP2020/064312 showing claim amendments.

* cited by examiner

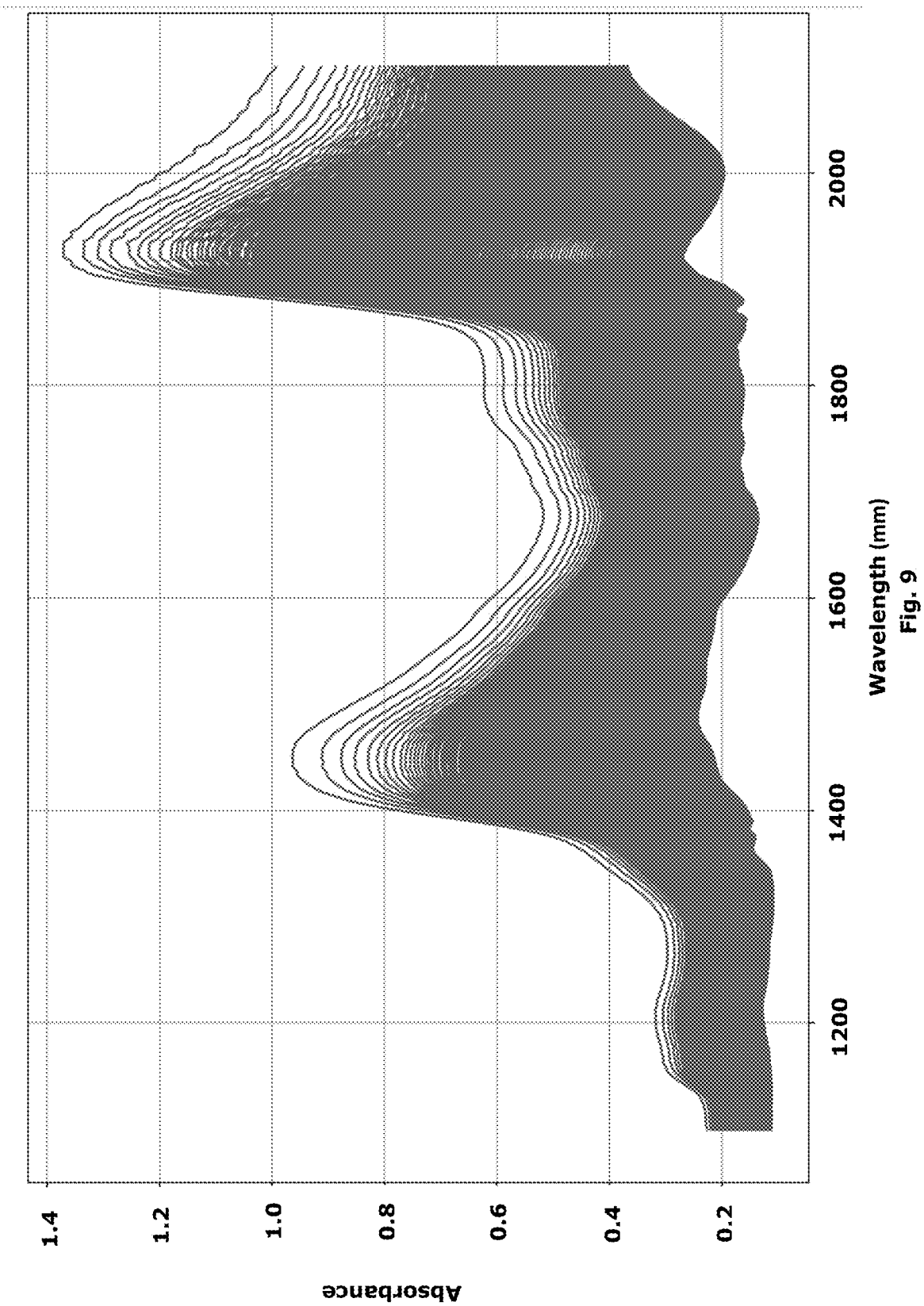

METHOD AND APPARATUS FOR DETERMINATION OF TEXTILE FIBER COMPOSITION

TECHNICAL FIELD

The invention pertains to the technical field of determination of fiber composition of textile samples (G01N 33/36) via spectroscopy, in particular near infrared (NIR) spectroscopy (G01N 21/359).

BACKGROUND

The volume and variety of materials in textile production are increasing. Textiles can be produced with a combination of fiber materials. An example is a textile with 50% cotton and 50% polyester, to combine the softness of cotton with the durability of polyester. Another example is a textile with 30% cotton and 70% polyester. Yet another example is a textile with 55% linen, 42% viscose and 3% spandex. One of ordinary skill in the art will appreciate that textile composition percentages are percentages by weight.

The Ellen MacArthur Foundation has published the document "*A new textiles economy: Redesigning fashion's future*" on 28 Nov. 2017. In present-day globalized consumer society, there is an overproduction of textiles, in combination with a decreasing second-hand market in third-world economies. Recycling is therefore primordial to realize a circular economy.

For recycling, it is important to correctly classify textile fiber composition. Higher-value recycling processes such as fiber recycling, polymer recycling or monomer recycling require input fractions with known fiber composition. Even in fabric recycling, where pieces of fabric are recombined to create new garments, the fiber composition must be known for correct labelling of the garments, and correct instruction for maintenance of the new garment.

Use of labels to classify textile composition is undesirable. Often labels are missing, or unreadable due to washing. In addition, there is no standardized location for attachment of a label. For automated classification and sorting, reading of labels should altogether be avoided. Furthermore, a label comprising a different textile fiber composition may have erroneously been attached to a garment.

Different tests for identification of textile fiber content are available. Examples include the burning test, the feeling test, the appearance test, the microscopic test, the solubility test, the optical test, the density test, and the dyeing test. For these tests, the selectivity is insufficiently high and/or the test is destructive in nature. The present invention seeks an alternative to the above-disclosed tests.

DE 199 20 592 A1 discloses analysis of a fibrous textile sample via NIR spectroscopy. The sample is subjected to the spectroscopy several times in short sequential periods. The result of each examination is evaluated using an artificial neural network (ANN) comprising nodes and weighted edges. The individual results of the ANN are used to create a global result, which is used to identify the sample.

U.S. Pat. No. 8,190,551 B2 discloses a method for classifying textile samples and unknown fabrics into known categories using spectroscopy, chemometric modeling, and soft independent modeling of class analogies (SIMCA). The method involves collecting spectral data, preferably diffuse NIR reflectance data, for a library of known fabric samples, creating a database of principal component analyses for each type of fabric, and using SIMCA to classify an unknown fabric sample according to the database. SIMCA can classify a sample as being in a single group, multiple groups, or not in any of the groups presented.

WO 2004/053 220 A1 discloses a method for the identification of a textile parameter from a soiled textile article in need of treatment. The surface of a soiled textile article is illuminated with electromagnetic radiation comprising a spectral range of from 783 nm to 1183 nm. Sample spectral data is collected from the surface of the textile article. The textile parameter is identified by comparing the sample of spectral data to reference spectral data obtained from a reference textile material, in particular via multivariate analysis.

The method according to U.S. Pat. No. 8,190,551 B2 would classify a textile comprising 30% cotton and 70% polyester as a material which tests positive regarding cotton and polyester content. However, the method according to U.S. Pat. No. 8,190,551 B2 is not suitable to accurately determine relative composition amounts for each of a plurality of fiber material types. In addition, the methods according to DE 199 20 592 A1 and WO 2004/053 220 A1 are also not suitable to accurately determine relative composition amounts for each of a plurality of fiber material types.

The present invention aims to resolve at least some of the problems mentioned above. The present invention in particular aims to accurately determine relative composition amount for each of a plurality of fiber material types. Another objective of the present invention is the sorting of textile samples, such as items of clothing, according to composition of fiber material types, in particular in a high throughput environment, e.g. for recycling.

SUMMARY OF THE INVENTION

In a first aspect, the present invention pertains to a method for determining a fiber composition of a textile sample, according to claim 1.

In a second aspect, the present invention pertains to an apparatus for determining a fiber composition of a textile sample, according to claim 14.

In a third aspect, the present invention pertains to use of the method according to the first aspect and/or use of the apparatus according to the second aspect for:
  sorting textile samples;
  production quality control; and/or
  composition label inspection.

One of ordinary skill in the art will appreciate that specific and particularly preferred examples of a "numerical relative composition amount" are a percentage by weight or a fraction by weight.

The present invention enables accurate determination of textile fiber composition, especially when a wide variety of fiber material types and compositions of fiber material types are targeted. The inventors have found that for an increasing amount of fiber material types and compositions of fiber material types, the training of a general unstructured artificial neural network (ANN) not only becomes exceedingly difficult, but also leads to a deterioration of classification results. Utilizing the deep neural network (DNN) as presently claimed, enables the inventors to simultaneously simplify the training process in terms of computer resources, and to outperform a general unstructured ANN in terms of accuracy. An exemplary general unstructured ANN comprises a weighted edge in between any two nodes (input, output and hidden), with a similar amount of weighted edges as the DNN. Further advantages, as well as advantages of preferred embodiments, are disclosed in the detailed description.

DESCRIPTION OF FIGURES

FIGS. 8 and 9 show spectra for a piece of cotton at different humidity levels.

DETAILED DESCRIPTION OF THE INVENTION

Figure 1:
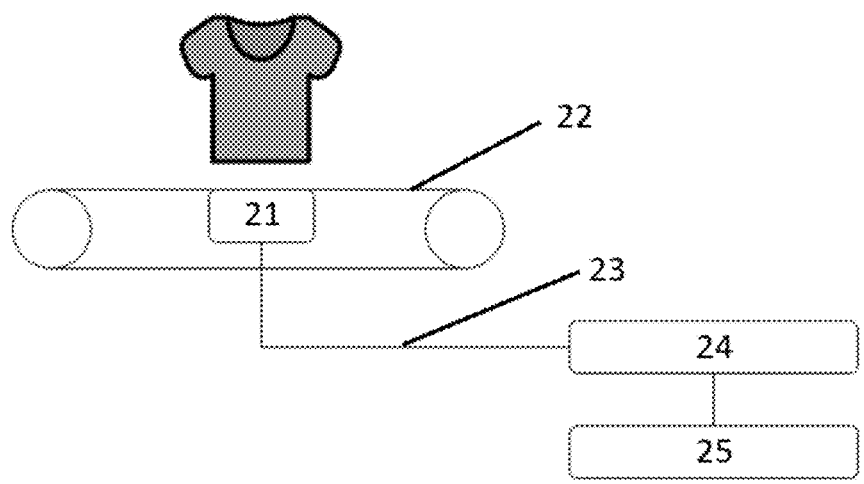
FIG. 1 shows a schematic overview of an embodiment of an apparatus according to the present invention.

The present invention concerns a method and an apparatus for determining a fiber composition of a textile sample, as well as several uses of the method and/or the apparatus. The invention has been summarized in the corresponding section above. In what follows, the invention is described in detail, preferred embodiments of the invention are discussed, and the invention is illustrated by means of non-limitative examples.

Term Definitions

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.

"Comprise", "comprising", "comprises" and "comprised of" as used herein are synonymous with "include", "including", "includes" or "contain", "containing", "contains" and are inclusive or open-ended terms that specify the presence of what follows (e.g. a component) and do not exclude or preclude the presence of additional, non-recited components, features, elements, members, steps, known in the art or disclosed therein.

The recitation of numerical ranges by endpoints includes all numbers and fractions subsumed within that range, as well as the recited endpoints.

Aspects of the Present Invention

In a first aspect, the present invention provides a method for determining a fiber composition of a textile sample. The method comprises several steps. The textile sample is irradiated with near infrared (NIR) light. Reflected NIR light from the sample is captured. A vector of spectral values is determined based on the captured light. The vector is input to a deep neural network (DNN). The DNN comprises a sequence of layers of nodes. The sequence comprises an input layer, at least two intermediate layers, and an output later. Nodes of successive layers of the sequence are interconnected via edges. Each edge comprises a weight, i.e. the edges are weighted edges. Output is obtained from the DNN. The output comprises for each of a plurality of fiber material types a numerical relative composition amount.

One of ordinary skill in the art will appreciate that specific and particularly preferred examples of a "numerical relative composition amount" are a percentage by weight or a fraction by weight.

In a second aspect, the present invention provides an apparatus for determining a fiber composition of a textile sample. The apparatus comprises a light source, a spectrometer, and a computer system. The light source is configured for irradiating the textile sample with near infrared (NIR) light. The spectrometer is configured for capturing reflected NIR light from the sample and determining a vector of spectral values based on the captured light. The computer system comprises at least one processor. The computer system is configured for obtaining the vector from the spectrometer, inputting the vector to a deep neural network (DNN), and obtaining output from the DNN. The DNN comprises a sequence of layers of nodes. The sequence comprises an input layer, at least two intermediate layers, and an output layer. Nodes of successive layers of the sequence are interconnected via edges. Each edge comprises a weight, i.e. the edges are weighted edges. The output comprises for each of a plurality of fiber material types a numerical relative composition amount. One of ordinary skill in the art will hence appreciate that the apparatus according to the second aspect is configured for performing the method according to the first aspect.

In a third aspect, the method according to the first aspect and/or the apparatus according to the second aspect may be used for any one or more of:

sorting textile samples (e.g. items of clothing, garments, carpets, table cloths, or fabrics in general), for example for recycling purposes or industrial cleaning, preferably for sorting waste textile samples such as waste textiles for re-use and/or recycling; and/or production quality control; and/or composition label inspection (e.g. at customs inspection).

One of ordinary skill in the art will appreciate that the three aspects of the present invention are hence interrelated. Each feature described above and/or below may therefore pertain to each aspect of the present invention, even if it has been described in conjunction with a particular aspect.

The present invention enables accurate determination of textile fiber composition, especially when a wide variety of fiber material types and compositions of fiber material types are targeted. The DNN outputs quantitative numerical relative composition amounts, for example percentages by weight, for each of a plurality of fiber material types. This allows not only to obtain qualitative presence of a particular fiber material type, e.g. whether cotton is present or not in the textile sample, but also a quantitatively accurate assessment of the particular relative amount. The inventors have found that for an increasing amount of fiber material types and compositions of fiber material types, the training of a general unstructured artificial neural network (ANN) not only becomes exceedingly difficult, but also leads to a deterioration of classification results. Utilizing the DNN as presently claimed, enables the inventors to simultaneously simplify the training process in terms of computer resources, and to outperform a general unstructured ANN in terms of accuracy. An exemplary general unstructured ANN comprises a weighted edge in between any two nodes (input, output and hidden), with a similar amount of weighted edges as the DNN.

Fiber Material Composition

One of ordinary skill in the art will appreciate that textile material composition "percentages" are "percentages by weight", and that textile material composition "fractions" are "fractions by weight". A textile sample comprising 30% cotton and 70% polyester, for example, comprises 30% by weight cotton and 70% by weight polyester. A textile sample comprising a fraction 0.30 cotton and 0.70 polyester, for example, comprises a fraction 0.30 by weight cotton and 0.70 by weight polyester.

A fiber material type may be a natural fiber material type or a synthetic fiber material type. In a preferred embodiment, the plurality of fiber material types comprises at least one natural fiber material type and at least one synthetic fiber material type.

A non-limiting exemplary list of textile fiber materials comprises abaca, acetate, acrylic (polyacrylonitrile), aramid (kevlar, nomex), bamboo, banana, coir, cotton, diacetate, hemp, jute, kapok, kenaf, leather, linen (flax), lyocell, modacrylic, modal, olefin, pina, polyamide (nylon), polyester, polyethylene (dyneema), polyvinylalcohol (vinylon), polyvinylchloride (vinyon), raffia, ramie, rayon (viscose), silk, sisal, soy protein, spandex (lycra, elastane), triacetate, wool, and blends thereof.

In a preferred embodiment, the plurality of fiber material types comprises at least two, preferably at least three, more preferably at least four, even more preferably at least five, and most preferably all six, of: a cotton type, a wool type, a polyester type, an acrylic type, a viscose type, and a polyamide type.

One of ordinary skill in the art will appreciate that "a genus type" may refer to the genus in general or a species of the genus in particular. For example, a polyamide type may refer to polyamide in general or nylon in particular. For example, a wool type may refer to wool in general or Alpaca wool in particular.

Near Infrared (NIR) Light

Near infrared (NIR) generally refers to light with wavelengths in the range of from 780 nm to 2500 nm.

NIR spectroscopy is a non-destructive analysis method, which does not require reagents or auxiliary chemicals. NIR light may penetrate 50 to 100 μm into the textile sample. The reflected light may therefore contain information on surface as well as bulk properties of the textile sample. NIR allows the simultaneous determination of multiple spectral values.

The captured reflected light may correspond to diffuse reflection or specular reflection. In a preferred embodiment, the captured reflected light corresponds to a diffuse reflection. Light from the light source may pass through a lens. In order to avoid light reflected from the lens to contribute to the analyzed reflection spectrum, a diffuse reflection is captured and analyzed. Thereto, the light source may be positioned under a different angle towards the textile sample than the capturing element.

The most prominent absorption bands occurring in the NIR region are related to the overtone bands which appear between about 780 and 2000 nm and combination bands of the fundamental molecular vibrations of C—H, N—H, O—H, and S—H functional groups which emerge between 1900 and 2500 nm. The electromagnetic spectrum between 1000 and 2500 nm is of most interest to the present invention and is in the prior art also referred to as short-wave-infrared (SWIR).

The inventors have initially tested a spectral range of from 900 nm to 1700 nm for the present invention, but soon came to the conclusion that the upper limit needed to be extended for textile fiber material types typical in used clothing. This is surprising in view of the range 783 to 1183 nm disclosed in WO 2004/053 220 A1.

Subsequently, the inventors investigated a spectral range of from 900 to 2500 nm, which was narrowed down to yield an accurate determination of textile fiber material composition, without overloading the data acquisition, processing, and deep neural network with an overly broad spectral range.

In a preferred embodiment, the vector comprises spectral values for wavelengths of at least 780 nm, preferably at least 900 nm, more preferably at least 1000 nm, and most preferably at least 1100 nm.

In a preferred embodiment, the vector comprises spectral values for wavelengths of at most 2500 nm, preferably at most 2400 nm, more preferably at most 2300 nm, even more preferably at most 2200 nm, yet even more preferably at most 2100 nm, and most preferably at most 2000 nm.

In a preferred embodiment, the vector comprises spectral values only for wavelengths in the range of 900 nm to 2400 nm, preferably in the range of 1000 nm to 2250 nm, even more preferably in the range of 1100 nm to 2100 nm, and most preferably in the range of 1100 nm to 2000 nm.

The inventors have found that such a reduced range allows for accurate fiber composition determination, while reducing the amount of data to be processed (both during composition determination as well as during training).

In a preferred embodiment, the vector comprises at least 32, preferably at least 64, more preferably at least 128, and most preferably at least 256, spectral values.

In a preferred embodiment, the vector comprises at most 65536, preferably at most 32768, more preferably at most 16384, even more preferably at most 8192, yet even more preferably at most 4096, with greater preference at most 2048, with even greater preference at most 1024, with yet even greater preference at most 512, and most preferably at most 256, spectral values.

The vector of spectral values comprises a constant or non-constant wavelength interval. An examples of a non-constant wavelength interval is a wavelength interval which appears constant on a logarithmic scale. In a preferred embodiment, the vector of spectral values comprises a constant wavelength interval.

In a preferred embodiment, the vector of spectral values comprises a wavelength interval of at most 10 nm, preferably at most 9 nm, more preferably at most 8 nm, even more preferably at most 7 nm, yet even more preferably at most 6 nm, with greater preference at most 5 nm, and with greatest preference at most 4 nm.

In a preferred embodiment, the vector of spectral values comprises sampled spectral values; or spectral values averaged or summed over a wavelength interval. In the latter case, the wavelength interval is also referred to as a band, and the size of the wavelength interval as a band width. Particularly preferred are spectral values corresponding to captured reflected light intensities over a band, or a function thereof.

The spectral values may be absolute values of amplitudes of captured reflected light, phases of amplitudes of captured reflected light, complex-valued amplitudes of captured reflected light, intensities of captured reflected light, or a function of any one or more of the preceding. In a preferred embodiment, the spectral values are intensities or a function of intensities of the captured reflected light. A particularly preferred function of intensities is a logarithm of the inverse of the intensities of the captured reflected light: $\log_y(1/R)$, wherein R is a vector with reflectance intensities for each of the wavelengths, and wherein y is the base of the logarithm, such as y=2, y=e or y=10.

In a preferred embodiment, the reflected light is guided through a narrow slit and collimating optics which rectify the light bundles towards a dispersing element such as a prism or grating in which the light is dispersed into a full spectrum of wavelengths. The dispersed light may be guided through focusing optics towards a detector. In a preferred embodiment, the NIR spectrum is captured in spectral values, each corresponding to the reflected light intensity in a narrow band of NIR wavelengths. For instance, if the spectrometer is configured to detect the spectrum from 1100 nm to 2100 nm with 256 data points, there will be 256 spectral values each corresponding to band width of (about) 3.91 nm.

In a preferred embodiment, a vector of spectral values is normalized based on calibration measurements. Preferably, the calibration measurements are regularly performed, at predefined moments in time. Preferably, the calibration measurements are performed at least once per day, more preferably at least once per 12 hours, even more preferably at least once per 6 hours, such as once per 4 hours, once per 3 hours, once per 2 hours, once per hour, once per 30 minutes, or once per 15 minutes. Preferably, the calibration measurements are based on a white and a black calibration reference. Herein, the white calibration reference may be an in essence fully reflective calibration item, such as a white plate. Herein, the black calibration reference may be an in essence fully absorbent calibration item, or an interruption of the optical circuit in between a passage for the textile sample and the spectrometer, such as an optical valve. For each of the white and black calibration references, a calibration vector of spectral values may be obtained. This may be performed via emitting NIR light, capturing reflected NIR light (if any), and determining the calibration vector based on the captured light. For an interruption of the optical circuit, the influence of noise may be determined. A vector of spectral values of a sample may then be normalized with the calibration vectors of spectral values for the black and white calibration references. One of ordinary skill in the art will appreciate that in this embodiment, the normalized vectors are input to the DNN. One of ordinary skill in the art will appreciate that in this embodiment, the normalized vectors are utilized for training the DNN.

In a preferred embodiment, the normalized vector of spectral values $R_n$ for a textile sample is $$R_n = -\log_y\left(\frac{R - R_b}{R_w - R_b}\right)$$

with
R the measured vector of spectral values for the textile sample;
$R_b$ the calibration vector of spectral values for the black calibration reference;
$R_w$ the calibration vector of spectral values for the white calibration reference.

Hardware

Preferably, the apparatus comprises a sensor head for capturing reflected light from a textile sample. Preferably, the apparatus comprises a fiber optic cable. Preferably, the fiber optic cable is positioned in between the sensor head and the spectrometer. Preferably, the fiber optic cable couples the sensor head to the spectrometer.

Preferably, the sensor head comprises a parabolic mirror. Preferably, the sensor head is configured for coupling captured reflected light into the fiber optic cable at or near the focal point of the parabolic mirror. Preferably, the spectrometer comprises a dispersing element and a detector. Preferably, the apparatus comprises a conveyer belt for transporting the textile sample. The apparatus may be configured to scan a textile sample while the textile sample is stationary with respect to the sensor head. Alternatively, the apparatus may be configured to scan a textile sample while the textile sample is moving via the conveyer belt. Preferably, the apparatus has a spectrum acquisition and analysis time of at most 50 milliseconds, more preferably at most 20 milliseconds, per textile sample. Preferably, the apparatus has a throughput of at least 0.2, more preferably at least 0.25, even more preferably at least 0.33, yet even more preferably at least 0.5, and most preferably at least 1, textile sample per second. One of ordinary skill in the art will appreciate that for the throughput, the transport time should also be taken into account. The apparatus may comprise one, two, three, four or more sensor heads. The apparatus may comprise one, two, three, four or more spectrometers. In case of multiple sensor heads, two sensor heads may be positioned at obverse sides of a passageway for a textile sample.

In a preferred embodiment, the apparatus comprises multiple conveyer belts and multiple sensor heads, whereby each sensor head is positioned at one of the multiple conveyer belts, whereby the multiple sensor heads are coupled to the spectrometer, whereby the apparatus comprises a multiplexer for switching between the sensor heads for sequential spectrum acquisition with each of the sensor heads. The spectrum acquisition and analysis time is typically significantly lower than the transport time for a textile sample. The computer system and spectrometer can be optimally used when textile samples on multiple conveyer belts are analyzed with the same computer system and spectrometer, sequentially in time.

Preferably, the black reference involves the interruption of light guidance from the textile sample to the spectrometer via an optical valve, such as a valve prior to the sensor head, a valve in between the fiber optic cable and the sensor head, or a valve in between the fiber optic cable and the spectrometer, for example.

In an embodiment, the apparatus may also comprise a color sensor system for detecting the color of a textile sample. The apparatus may in this case be configured for sorting the textile samples based at least in part on color.

In an embodiment, the apparatus may also comprise a texture sensor system for detecting the texture of a textile sample, e.g. whether a textile sample is woven or knitted. The texture sensor system may comprise a camera and/or a distance sensor. The apparatus may in this case be configured for sorting the textile samples based at least in part on texture.

Preferably, one vector of spectral values is determined per textile sample. Preferably, a single vector of spectral values is determined per textile sample. Preferably, at most one vector of spectral values is determined per textile sample.

In a preferred embodiment, the apparatus comprises multiple spatially separated output locations. The apparatus may be configured for determining an output location based on the output of the artificial neural network and transporting the textile sample to the determined output location. Each output location may comprise a bin.

In a preferred embodiment, a composition category from a group of composition categories is selected for the textile sample based on the numerical relative composition amounts of the output. A non-limitative exemplary list of composition categories may comprise: 0% cotton and 100% polyester; 5% cotton and 95% polyester; 10% cotton and 90% polyester; 15% cotton and 85% polyester; 20% cotton and 80% polyester; 25% cotton and 75% polyester; and the like. For a textile sample with determined numerical relative composition amounts 19.8% cotton, 79.4% polyester and 0.8% remainder, for example, the category 20% cotton and 80% polyester may be selected, for example. Preferably, each output location corresponds with one or more composition categories.

Measurements may be performed with the sensor head at distances of between 150 and 600 mm from the textile sample. The sensor head may be positioned below the textile sample in the plane of the conveyer belt, or above the textile sample. Preferably, the reflection sensor head is connected to the spectrometer via a fiber optic cable. The fiber optic cable should be of sufficient quality. The inventors have found that the fiber optic cable should contain as few OH groups as possible, as such groups are responsible for water absorbance. Water absorbance by the fiber optic cable disturbs the spectrum of interest, in particular for textile fiber composition determination. When multiple apparatuses according to the present invention are utilized, it is important to keep the length of the fiber optic cable constant over the multiple apparatuses. An exemplary length of the fiber optic cable, utilized by the inventors, is about 10 m.

Structure of the DNN

The DNN comprises a sequence of layers of nodes. The sequence comprises an input layer, at least two intermediate layers, and an output layer. Nodes of successive layers of the sequence are interconnected via edges. Each edge comprises a weight. The edges are hence weighted edges.

Most preferably, the DNN comprises edges only in between nodes of successive layers. Most preferably, each edge of the DNN connects two nodes of successive layers.

Most preferably, the DNN does not comprise a weighted edge directly connecting a node of the input layer with a node of the output layer.

A "deep neural network" (DNN) is computer-implemented. The DNN comprises computer-processable, preferably digital, data which represents the nodes, edges and edge weights. A non-limiting exemplary list of deep learning software, i.e. computer program products for deep learning, comprises Accord.NET, Apache MXNet, Apache SINGA, BigDL, Caffe, Chainer, Deeplearning4j, Dlib, Intel Data Analytics Acceleration Library, Keras, Matlab Deep Learning Toolbox, Microsoft Cognitive Toolkit (CNTK), Neural Designer, OpenNN, PyTorch, scikit-learn, TensorFlow, Theano, Torch, and Wolfram Mathematica.

A preferred computer program product for deep learning is Microsoft Cognitive Toolkit (CNTK), such as version 2.6 with Graphical Processing Unit support. Such a computer program product allows for representing the DNN, training the DNN, and utilizing the DNN to obtain for each of a plurality of fiber material types a numerical relative composition amount (e.g. percentage by weight) by inputting a vector of spectral values.

In a preferred embodiment, the sequence of layers of the DNN comprises at least three, more preferably at least four, most preferably at least five, intermediate layers.

In a preferred embodiment, the sequence of layers of the DNN comprises at most 1024, preferably at most 512, more preferably at most 256, even more preferably at most 128, yet even more preferably at most 64, with even greater preference at most 32, and most preferably at most 16, intermediate layers. The sequence may comprise 5, 6, 7, 8, 9, 10, 11, 12, 13, 14, 15 or 16 intermediate layers, for example. More preferably, the sequence comprises 5, 6, 7 or 8 intermediate layers. Most preferably, the sequence comprises 5 intermediate layers.

The DNN is configured to provide via the weighted edges to each successive layer the output from the previous layer as input. An artificial neural network may or may not comprise feedback loops. Preferably, the DNN is a feedforward network. Preferably, the DNN does not comprise feedback loops. Preferably, the DNN is configured for data flow from the input layer to the output layer without looping back. Preferably, the DNN is a non-recurrent neural network.

In a preferred embodiment, the number of nodes in successive layers does not increase from the input layer to the output layer.

A pair of successive layers of the sequence may comprise the same number of nodes.

A node may or may not comprise an activation function. The activation function may be a linear activation function or a non-linear activation function. A linear activation function may be $f(x)=x$. In a preferred embodiment, the nodes of an intermediate layer comprise a non-linear activation function. Preferably, the nodes of each intermediate layer comprise a non-linear activation function. Preferably, the non-linear activation function is:

a rectified linear unit activation function $f(x)=\max(0, x)$;
a softplus activation function $f(x)=\log_e(1+e^x)$;
a binary step activation function $f(x)=\{0$ for $x<0$; $1$ for $x\geq 0\}$;

a sigmoid (logistic) activation function $f(x) = \frac{1}{1+e^{-x}}$; or

-continued a hyperbolic tangent activation function $f(x) = \tanh(x) = \frac{e^x - e^{-x}}{e^x + e^{-x}}$.

Herein, f(x) is the output of a node and x is the sum of incoming signals, i.e. the sum of outputs of the nodes of the previous layer multiplied with the weights of the edges connecting the nodes of the previous layer with this node. More preferably, the non-linear activation function is a hyperbolic tangent activation function or a sigmoid activation function. Most preferably, the non-linear activation function is a hyperbolic tangent activation function.

At least some of the nodes of a layer of a pair of successive layers are connected via a weighted edge with one or more other nodes of the other layer of the pair. In a preferred embodiment, each node of a layer of a pair of successive layers is connected via a weighted edge with each node of the other layer of the pair, i.e. the layers of the pair are "fully interconnected". Preferably, all pairs of successive layers of the sequence are fully interconnected, i.e. the DNN comprises "dense layers".

In a preferred embodiment, the input layer corresponds to the vector of spectral values. Preferably, the number of nodes of the input layer is equal to the number of spectral values of the vector.

In a preferred embodiment, the output layer corresponds to the plurality of fiber material types augmented with a remainder type. Preferably, the number of nodes of the output layer is equal to the number of fiber material types of the plurality plus one.

Training of the DNN

The DNN may be trained via a multitude of training textile samples comprising a known training composition of fiber material types. Preferably, at least several training textile samples of the multitude comprise a training composition of two or more fiber material types. A training textile sample may comprise one, two, three, four, five, six, seven, eight, nine or more fiber material types. A training textile sample may comprise a composition comprising a fiber material type not present in said plurality of fiber material types. Most preferably, the multitude comprises two or more training textile samples comprising the same fiber material types but in different relative amounts. For example, a first training textile sample may comprise 50% cotton and 50% polyester and a second training textile sample may comprise 30% cotton and 70% polyester. Different compositions may hence differ in the fiber material type and/or in the relative amount of certain fiber material types. Preferably, the multitude of training textile samples comprises a set of samples with an identical fiber composition, but with different humidity level, different coating, different color and/or different texture over the samples of the set. Humidity level, coating, color and texture may influence the NIR spectrum. For correct identification of the composition, the DNN may therefore be trained with training textile samples with identical fiber material composition, but differing in other features, such as humidity level, coating, color and/or texture.

For each training textile sample of the multitude, a vector of spectral values may be obtained, via irradiating the sample with NIR light, capturing reflected NIR light from the sample, and determining the vector based on the captured light. The DNN may then be trained with the vector of spectral values and the training composition of each training textile sample of the multitude.

In a preferred embodiment, the training of the DNN is performed via an iterative optimization of the weights of the edges. Preferably, the iterative optimization is performed during a predefined number of iterations or until a predefined accuracy is reached. Preferably, training textile samples of the multitude are labelled either as modelling or testing samples. The modelling samples may be used to calculate a first set of weights of the DNN. Then, the weights may be iteratively updated by making a prediction for testing samples, comparing the prediction with the known training composition of the testing samples, and updating the weights of the DNN.

In a preferred embodiment, the weights are updated using gradient descent. The gradient descent may be stochastic gradient descent, batch gradient descent, or mini-batch gradient descent. Preferably, the weights are updates using mini-batch gradient descent, in which weights are iteratively updated based on the predictions for an incomplete subset of testing samples.

Preferably, the multitude comprises at least 1000, more preferably at least 2000, even more preferably at least 4000, and most preferably about 8000, training textile samples.

Preferably, training is performed for a plurality of iterations until the accuracy saturates, such as at or near the onset of overfitting. Exemplary numbers of iterations the inventors have utilized range from 50 iterations, for simple spectra in combination with a small number of fiber material types in the plurality of fiber material types, to 2000 iterations, for a plurality comprising six fiber material types.

Preferably, the number of training textile samples for each composition is at least 5, preferably at least 10, more preferably at least 20, such as 20, 24, 28, 32, 36, 40, 44, 48 or 50. Most preferably, the number of textile samples per composition is at least 40, such as about 50.

EXAMPLES

The invention is further described by the following non-limiting examples which further illustrate the invention, and are not intended to, nor should they be interpreted to, limit the scope of the invention.

Example 1: Apparatus

The present example pertains to an embodiment of an apparatus according to the present example.

FIG. 1 shows a schematic overview of the embodiment. The apparatus comprises a conveyor belt (22), a sensor head (21) comprising a light source, a lens and a capturing element, a fiber optic cable (23), a spectrometer (24), and a computer system (25). The fiber optic cable couples the sensor head to the spectrometer. Shown in the figure is a sensor head positioned in the plane of the conveyor belt. Alternatively, the sensor head may be positioned above the conveyor belt to scan textile samples from above.

The apparatus is configured for capturing diffuse reflections of NIR light from the textile sample. The reflected light is guided through a narrow slit and collimating optics which rectify the light bundles towards a dispersing element such as a prism or grating in which the light is dispersed into a full spectrum of wavelengths. The dispersed light is guided through focusing optics towards a detector. The NIR spectrum is captured in spectral values, each corresponding to a reflected light intensity in a narrow band of NIR wavelengths. The spectrometer is in particular configured to detect the spectrum from 1100 nm to 2100 nm with 256 data points. The vector hence comprises 256 spectral values each corresponding to a band width of about 3.91 nm. Most preferably, the spectral values are a logarithm of the inverse of the captures reflected light intensities, as described in the detailed description.

The computer system is configured for obtaining the vector from the spectrometer and for determining the numerical relative composition amounts for each of a plurality of fiber material types. The plurality may in particular comprise acrylic, cotton, polyamide, polyester, viscose and wool.

Example 2: Deep Neural Network

The present example pertains to a deep neural network (DNN). The present example preferably pertains to previous example 1. The inventors have used Microsoft Cognitive Toolkit (CNTK) version 2.6 with Graphical Processing Unit support for their embodiment of the present invention, but other computer program products may of course be utilized.

The DNN of the present invention is a feedforward network, which is configured for data flow from an input layer to an output layer without looping back. The DNN comprises an input layer of 256 nodes, five intermediate layers, and an output layer of 7 nodes. The intermediate layers comprise, from input layer to output layer, respectively 256, 128, 64, 32 and 16 nodes. All pairs of successive layers are fully interconnected. Each node of a layer of each pair is hence connected via an edge with each node of the other layer of the pair. Each edge comprises a weight.

The number of nodes of the input layer is in number equal to the number of spectral values of a vector. The number of nodes of the output layer is in number equal to the number of fiber material types in the plurality, augmented with one for the remainder type.

Example 3: Data Processing Algorithm

The present example pertains to an embodiment of a data processing algorithm according to the present invention. The present example preferably pertains to previous example 1. The present example preferably pertains to previous example 2.

Figure 2:
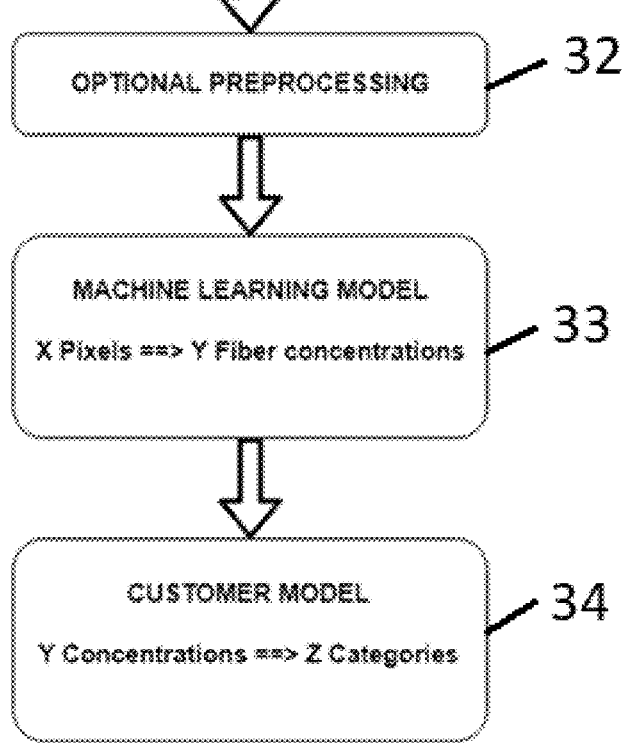
FIG. 2 shows a schematic overview of an embodiment of a data processing algorithm according to the present invention.

FIG. 2 shows a schematic overview of the embodiment.

A vector of spectral values (31) is obtained for a textile sample. The vector may optionally be preprocessed (32). The preprocessing may comprise normalizing the vector based on calibration vectors, such as described in the detailed description above. The vector is input to a trained DNN, such as a DNN according to example 2, which converts the vector to a numerical relative composition value for each of a plurality of material types (33). Such conversion provides continuous relative composition values. One of ordinary skill in the art will appreciate that in the context of the present invention "continuous" refers to floating point representation on a computer system. Based on the numerical relative composition values, one of a plurality of categories is selected (34). A category may comprise a set of numerical relative composition values. The category may be selected based on 2-norm difference for the respective numerical relative composition values. Such selection provides one category of a discrete set of pre-defined categories.

Example 4: Training the DNN

The present example pertains to an embodiment of a training algorithm according to the present invention. The present example preferably pertains to previous example 1. The present example preferably pertains to previous example 2. The present example preferably pertains to previous example 3.

The DNN is trained according to all preferred embodiments of the corresponding section in the detailed description. The multitude of training textile samples in particular comprises training samples:
 some of which have different fiber material types;
 some of which have multiple fiber material types;
 some of which have the same (multiple) fiber material types, but in different relative amounts; and
 some of which have the same fiber material types and the same composition of fiber material types, but have different humidity level, coating, color and/or texture.

The multitude comprises 8000 or more training samples, and at least 40 (and in particular about 50 training samples) per targeted composition category.

Preferably, the nodes of the output layer comprise a softmax activation function, and the training objective is based on a categorical cross-entropy objective.

Preferably, the update is based on gradient descent with Nesterov momentum, in particular with a momentum parameter of 0.9 and a learning rate 0.01.

Preferably, the mini-batch size is 8.
Preferably, the number of training epochs is 2000.

Example 5: Exemplary Spectra

Figure 3:
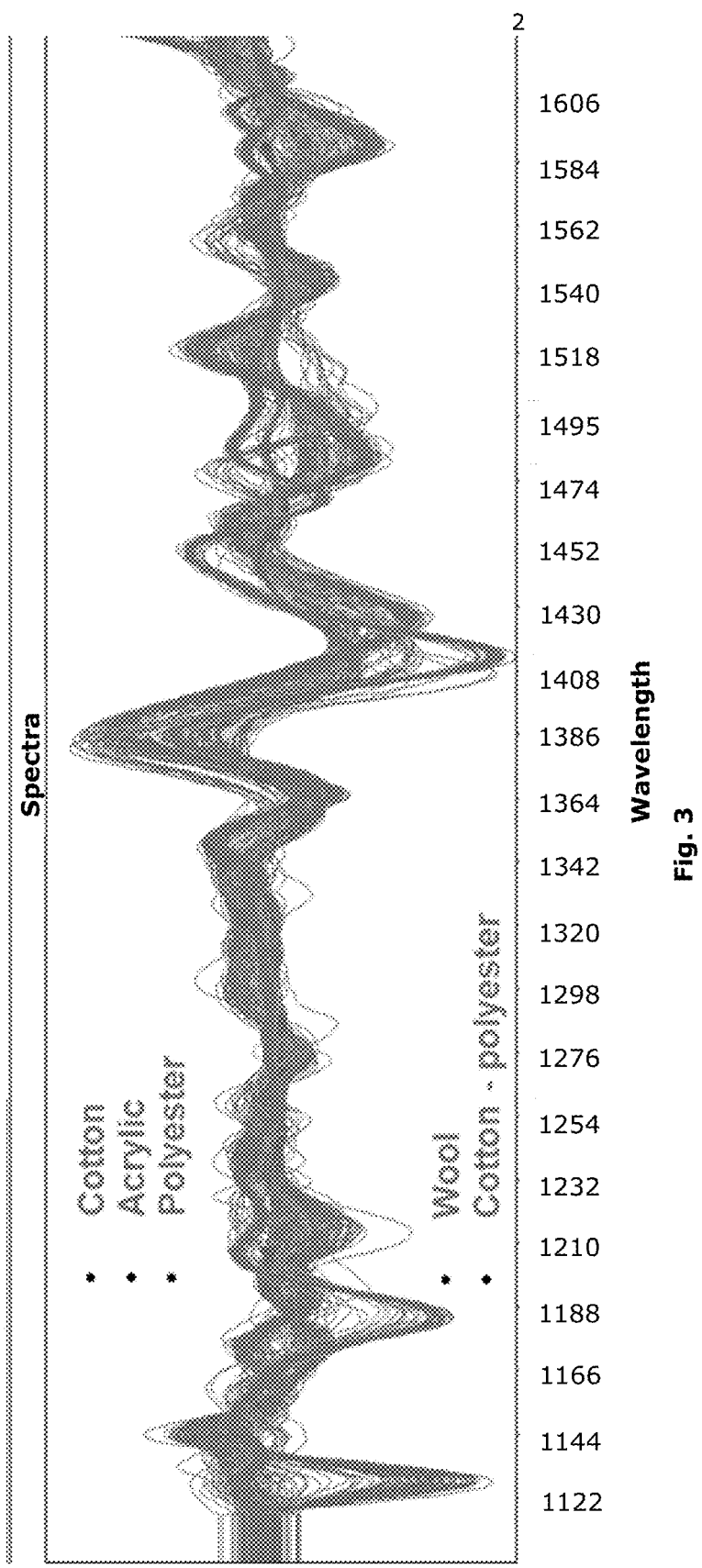
FIGS. 3, 4 and 5 show exemplary spectra of textile samples, in order to illustrate several features of a data processing algorithm according to the present invention.
Figure 4:
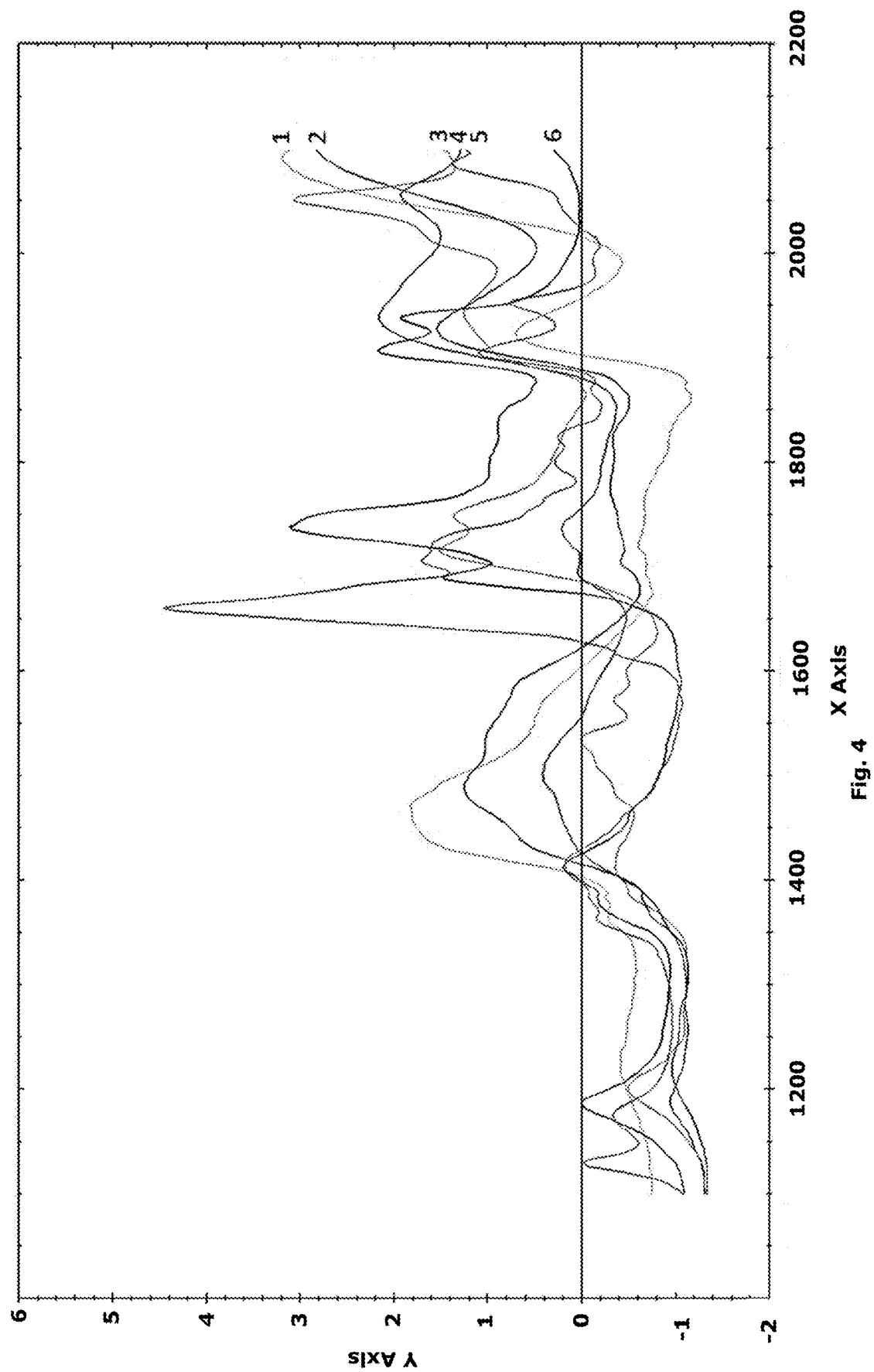
Figure 5:
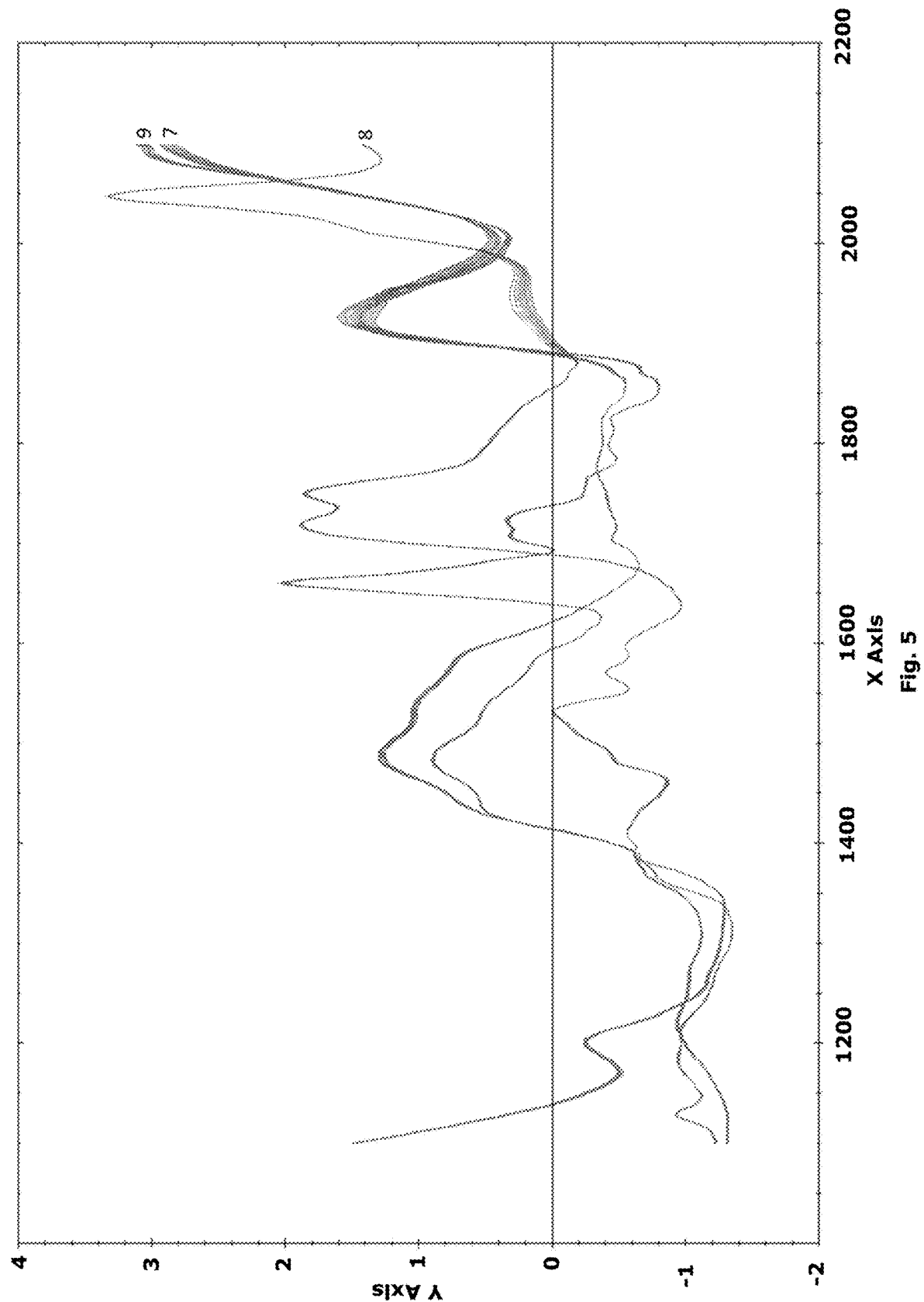

FIGS. 3, 4 and 5 show exemplary spectra of textile samples.

FIG. 3 shows a particular wavelength region (wavelengths in nm), illustrating that in the particular region shown, the various fiber material types exhibit characteristic peaks, but that different samples with the same composition still exhibit quite some variation. This might be due to differences in humidity level, color, coating and/or texture.

FIG. 4 shows several spectra of pure textile samples. Spectrum (1) corresponds with pure viscose, spectrum (2) with pure cotton, spectrum (3) with pure nylon (polyamide), spectrum (4) with pure wool, spectrum (5) with pure polyester, and spectrum (6) with pure acrylic.

FIG. 5 shows several spectra corresponding with pure cotton (7), several spectra corresponding with pure polyester (8), and several spectra corresponding with blended textile samples comprising 55% cotton and 45% polyester. As can be observed, the blended textile samples are not a mere superposition of the pure textile samples, indicating the need for training the DNN with blended textile samples.

Example 6: First Comparative Example

The present example pertains to all of the above examples 1, 2, 3 and 4.

Tables 1 and 2 show composition percentages by weight for pure textile samples, i.e. comprising one fiber material type, obtained according to the present invention and obtained via prior art correlation modelling, such as disclosed in U.S. Pat. No. 8,190,551 B2, respectively.

TABLE 1

Composition for pure textile samples: present invention.

| Sample | Cotton | Polyester | Wool | Acrylic | Viscose | Polyamide |
|---|---|---|---|---|---|---|
| 598 (cotton) | 99% | 1% | 0% | 0% | 0% | 0% |
| 599 (polyester) | 0% | 98% | 0% | 0% | 0% | 0% |
| 600 (wool) | 0% | 0% | 100% | 0% | 0% | 0% |

TABLE 1-continued

Composition for pure textile samples: present invention.

| Sample | Cotton | Polyester | Wool | Acrylic | Viscose | Polyamide |
|---|---|---|---|---|---|---|
| 601 (acrylic) | 0% | 0% | 0% | 99% | 0% | 0% |
| 602 (viscose) | 0% | 0% | 0% | 0% | 99% | 0% |
| 603 (nylon) | 0% | 0% | 0% | 0% | 0% | 99% |

TABLE 2

Composition for pure textile samples: prior art.

| Sample | Cotton | Polyester | Wool | Acrylic | Viscose | Polyamide |
|---|---|---|---|---|---|---|
| 598 (cotton) | 100% | 9% | 84% | 20% | 96% | 63% |
| 599 (polyester) | 14% | 100% | 29% | 49% | 23% | 33% |
| 600 (wool) | 88% | 26% | 99% | 52% | 94% | 85% |
| 601 (acrylic) | 20% | 44% | 47% | 100% | 32% | 61% |
| 602 (viscose) | 80% | −2% | 53% | −10% | 72% | 38% |
| 603 (nylon) | 66% | 33% | 86% | 67% | 72% | 99% |

Although correlation modelling would still allow to sort pure fibers based upon a certain threshold level for the correlation factor, the present invention clearly outperforms the correlation modelling, and the analysis will become much more complicated when different compositions need to be discerned.

Example 7: Second Comparative Example

The present example pertains to all of the above examples 1, 2, 3 and 4.

Tables 3, 4 and 5 show composition percentages by weight for blended textile samples, i.e. comprising multiple fiber material types, obtained according to the present invention, obtained via prior art correlation modelling, such as disclosed in U.S. Pat. No. 8,190,551 B2, and obtained via chemical analysis, respectively.

TABLE 3

Composition for blended textile samples: present invention.

| Sample | Cotton | Polyester | Wool | Acrylic | Viscose | Polyamide |
|---|---|---|---|---|---|---|
| 601 (acrylic) | 0% | 0% | 0% | 100% | 0% | 0% |
| 606 (wool) | 0% | 0% | 97% | 0% | 0% | 0% |
| 619 (wool 30%, acrylic 70%) | 1% | 1% | 29% | 69% | 1% | 0% |
| 616 (wool 50%, acrylic 50%) | 0% | 0% | 51% | 48% | 0% | 0% |

TABLE 4

Composition for blended textile samples: prior art.

| Sample | Cotton | Polyester | Wool | Acrylic | Viscose | Polyamide |
|---|---|---|---|---|---|---|
| 601 (acrylic) | 20% | 44% | 47% | 100% | 32% | 61% |
| 606 (wool) | 88% | 25% | 100% | 52% | 94% | 84% |
| 619 (wool 30%, acrylic 70%) | 81% | 26% | 98% | 56% | 87% | 88% |
| 616 (wool 50%, acrylic 50%) | 84% | 29% | 99% | 63% | 91% | 88% |

TABLE 5

Composition for blended textile samples: chemical analysis.

| Sample | Wool | Acrylic |
|---|---|---|
| 601 (acrylic) | / | 97% |
| 606 (wool) | / | / |
| 619 (wool 30%, acrylic 70%) | 30% | 70% |
| 616 (wool 50%, acrylic 50%) | 54% | 46% |

The methods according to the present invention yield accurate results. Traditional correlation methods show a high correlation with wool, and a poor correlation with acrylic. This renders traditional correlation methods unsuitable for the envisaged sorting application.

Example 8: Third Comparative Example

The present example pertains to all of the above examples 1, 2, 3 and 4.

Table 6 show composition percentages by weight for blended textile samples, i.e. comprising multiple fiber material types, predicted (pred.) according to the present invention (columns 2 and 3) and obtained via chemical (chem.) analysis (columns 4 and 5).

The predicted composition according to the present invention matches the results obtained by chemical analysis to a high degree of accuracy. This renders the present invention suitable for the envisaged sorting application.

TABLE 6

Composition for blended textile samples: prediction according to the present invention and chemical analysis.

| Sample | Cotton (pred.) | Polyester (pred.) | Cotton (chem.) | Polyester (chem.) |
|---|---|---|---|---|
| 65542 | 100.0% | 0.0% | 100.0% | 0.0% |
| 65543 | 100.0% | 0.0% | 100.0% | 0.0% |
| 65541 | 100.0% | 0.0% | 100.0% | 0.0% |
| 65540 | 100.0% | 0.0% | 100.0% | 0.0% |
| 65539 | 100.0% | 0.0% | 100.0% | 0.0% |
| 65538 | 100.0% | 0.0% | 100.0% | 0.0% |
| 65537 | 100.0% | 0.0% | 100.0% | 0.0% |
| 66304 | 91.5% | 8.5% | 90.0% | 10.0% |
| 66305 | 91.5% | 8.5% | 90.0% | 10.0% |
| 66306 | 91.6% | 8.4% | 90.0% | 10.0% |
| 66309 | 91.6% | 8.4% | 90.0% | 10.0% |
| 66308 | 91.6% | 8.4% | 90.0% | 10.0% |
| 65614 | 83.1% | 16.9% | 80.0% | 20.0% |
| 65685 | 83.3% | 16.6% | 80.0% | 20.0% |
| 65613 | 83.6% | 16.4% | 80.0% | 20.0% |
| 65668 | 76.3% | 22.1% | 80.0% | 20.0% |
| 68519 | 70.8% | 29.1% | 72.0% | 28.0% |
| 68525 | 75.9% | 24.0% | 72.0% | 28.0% |
| 68920 | 66.2% | 33.0% | 70.0% | 30.0% |
| 66009 | 70.8% | 29.2% | 70.0% | 30.0% |
| 68450 | 64.2% | 35.8% | 65.0% | 35.0% |
| 68449 | 64.4% | 35.6% | 65.0% | 35.0% |

TABLE 6-continued

Composition for blended textile samples:
prediction according to the present invention and chemical analysis.

| Sample | Cotton (pred.) | Polyester (pred.) | Cotton (chem.) | Polyester (chem.) |
|---|---|---|---|---|
| 68478 | 58.0% | 42.0% | 60.0% | 40.0% |
| 65610 | 58.3% | 41.4% | 60.0% | 40.0% |
| 66357 | 57.2% | 42.8% | 55.0% | 45.0% |
| 68322 | 49.6% | 50.4% | 50.0% | 50.0% |
| 68321 | 49.6% | 50.4% | 50.0% | 50.0% |
| 66334 | 34.6% | 65.4% | 35.0% | 65.0% |
| 66340 | 34.7% | 65.3% | 35.0% | 65.0% |
| 68403 | 34.8% | 65.2% | 35.0% | 65.0% |
| 68402 | 34.8% | 65.2% | 35.0% | 65.0% |
| 66219 | 34.9% | 65.1% | 35.0% | 65.0% |

Example 9: Sorting Apparatus

Figure 6:
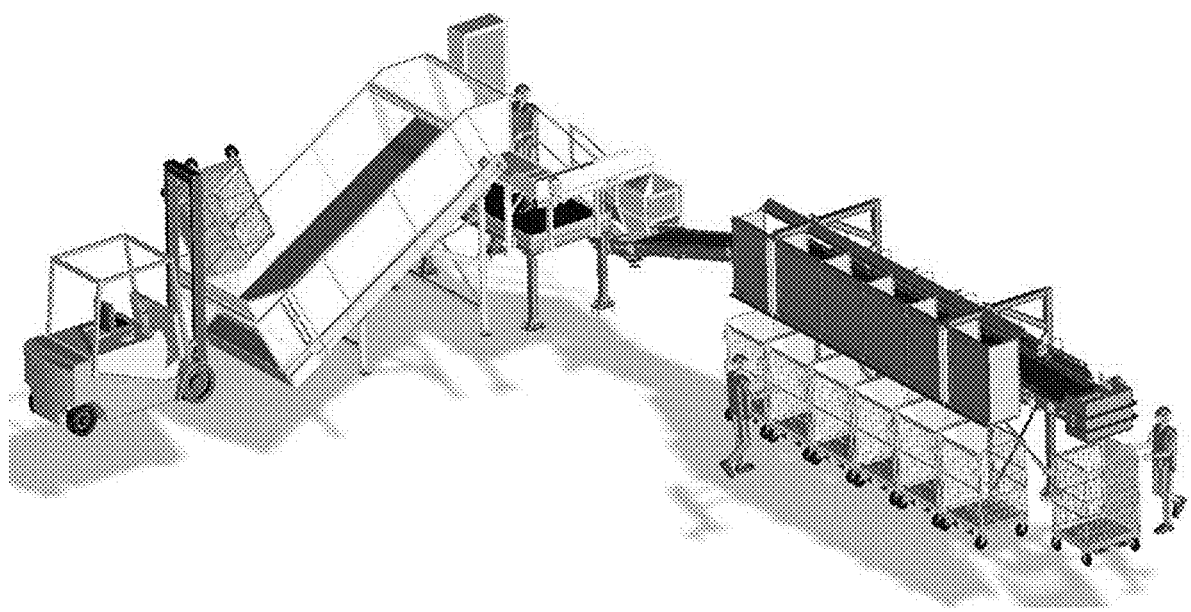
FIG. 6 shows a schematic overview of an embodiment of an apparatus according to the present invention, configured for sorting textile samples, such as items of clothing, according to fiber composition.

FIG. 6 shows a sorting apparatus according to all of the preceding examples 1, 2, 3 and 4. The apparatus comprises multiple output locations. The apparatus is configured for determining an output location based on the output of the deep neural network and transporting the textile sample to the determined output location. In the present example, bins comprising wheels are provided at each output location, for deposit of textile samples. The apparatus according to the present example is particularly suitable for sorting purposes, e.g. prior to recycling.

Example 10: Adaptiveness

Upon identifying a wrongly categorized textile sample, or a textile sample comprising a novel fiber material type and/or composition, the textile sample may be added to the training set. This renders the method and apparatus according to the present invention suitable for tailoring the invention to each particular need, and for continuous learning.

Example 11: Structure DNN

The present example pertains to all of the above examples 1, 2, 3 and 4.

Figure 7:
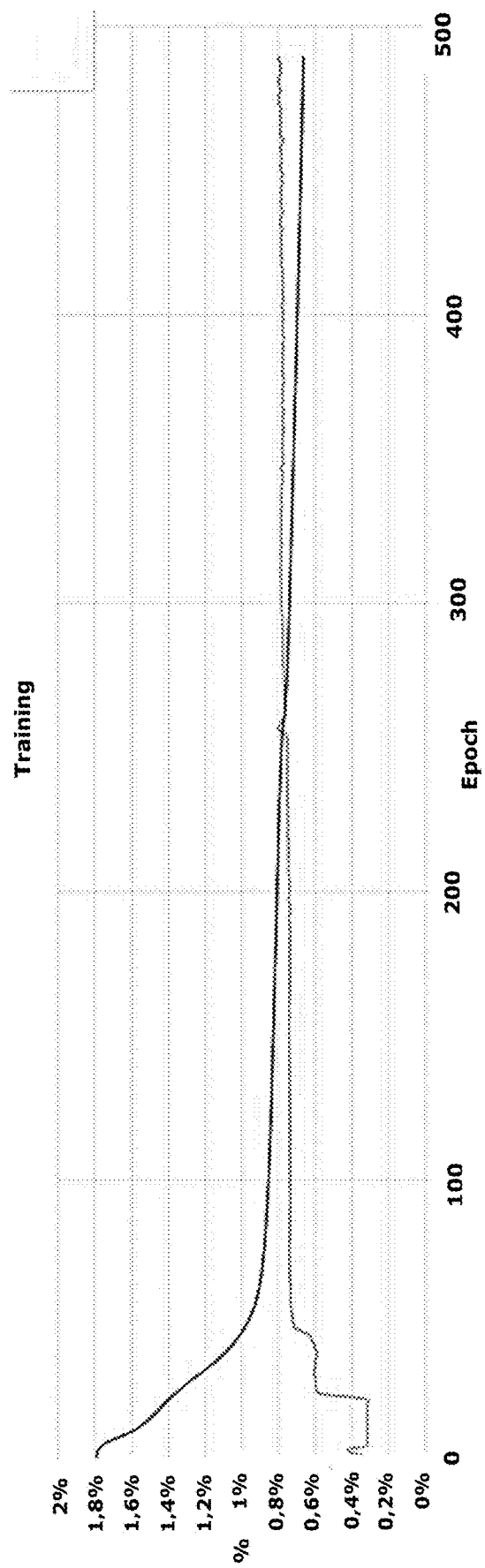
FIG. 7 shows an increase in accuracy with minimization of a loss of function for DNN with a single intermediate layer.

FIG. 7 shows an increase in accuracy with minimization of a loss function for a DNN with a single intermediate layer. The accuracy starts plateauing after 60-70 epochs of training at about 75%. After 480 epochs of training, the accuracy reaches 83.2%. The above experiment was repeated for DNNs with an increasing number (1 to 5) of intermediate layers and a decreasing number of nodes in each subsequent layer. The results after 480 epochs of training are shown below.

TABLE 7

Accuracy using different DNN structures:

| 1 | 8 | 83.2% |
| 2 | 32 - 8 | 84.1% |
| 3 | 64 - 32 - 8 | 86.3% |
| 4 | 128 - 64 - 32 - 8 | 88.9% |
| 5 | 256 - 128 - 64 - 32 - 8 | 90.2% |

Example 12: Humidity Level

The present example pertains to all of the above examples 1, 2, 3 and 4.

Figure 8:
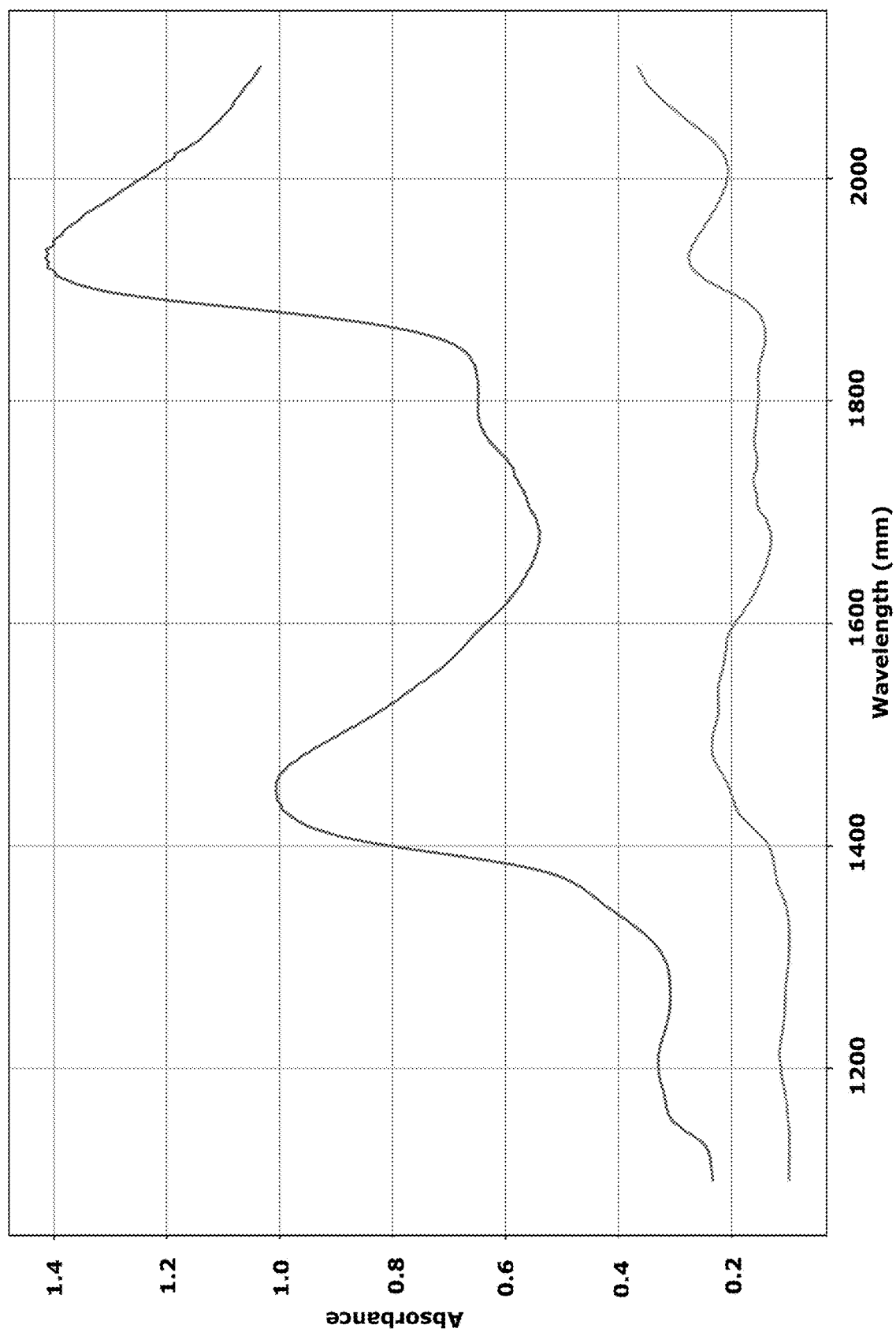

FIGS. 8 and 9 show spectra for a piece of cotton at different humidity levels. As can be observed, the samples show an absorbance increase and shift with an increase in moisture level. This indicates the need for training the DNN with textile samples with a different moisture content. This is particularly relevant for sorting waste textile samples such as waste textiles for re-use or recycling.

Similar experiments were performed for textile samples with a different coating, color and/or texture, yielding similar results, and thereby also indicating the need for training the DNN with textile samples with different coatings and textures. This is also particularly relevant for sorting waste textile samples such as waste textiles for re-use or recycling.

The invention claimed is:

1. A method for determining a fiber composition of a textile sample, comprising the steps of:
   moving the textile sample relative to a test point using an apparatus comprising a means for transporting the textile sample;
   irradiating the textile sample with near infrared light at the test point while the textile sample is moving relative to the test point via the transporting means;
   capturing reflected near infrared light from the textile sample at the test point while the textile sample is moving relative to the test point via the means for transporting the textile sample;
   determining a vector of spectral values based on the captured light;
   inputting the vector to an artificial neural network comprising nodes and edges, wherein each edge comprises a weight; and
   obtaining output from the artificial neural network,
   wherein the artificial neural network is a deep neural network comprising a sequence of layers of nodes, wherein the sequence comprises an input layer, at least two intermediate layers and an output layer, wherein nodes of successive layers of the sequence are interconnected via weighted edges, wherein the deep neural network is a feedforward neural network which is configured for data flow from the input layer to the output layer without looping back,
   wherein the output from the artificial neural network comprises for each of a plurality of fiber material types a numerical relative composition amount,
   wherein the method comprises the additional steps of:
   obtaining a vector of spectral values for each training textile sample of a multitude of training textile samples, wherein each of the plurality of fiber material types is present in at least one of the multitude of training textile samples, wherein at least several training textile samples of the multitude comprise a training composition of two or more fiber material types, via:
   irradiating the training textile sample with near infrared light,
   capturing reflected near infrared light from the training textile sample, and
   determining the vector based on the captured light;
   training the deep neural network with the vector of spectral values and a training composition of each training textile sample of the multitude,
   wherein, the multitude of training textile samples comprises a set of training textile samples with an identical fiber composition and with different humidity level, different coating, different color and/or different texture over the training textile samples of the set.

2. The method according to claim 1, wherein the captured reflected light corresponds to a diffuse reflection.

3. The method according to claim 1, wherein the deep neural network is configured according to one, two, three or all four of the following:
- the sequence comprises at least three, preferably at least four, most preferably at least five, intermediate layers;
- the number of nodes in successive layers does not increase from the input layer to the output layer;
- the nodes of an intermediate layer comprise a non-linear activation function, preferably a sigmoid activation function or a hyperbolic tangent activation function, most preferably a hyperbolic tangent activation function;
- each node of a layer of a pair of successive layers is connected via a weighted edge with each node of the other layer of the pair.

4. The method according to claim 1, wherein the vector comprises spectral values only for wavelengths in the range of 900 nm to 2400 nm.

5. The method according to claim 1, wherein the vector of spectral values comprises a constant wavelength interval.

6. The method according to claim 1, wherein the vector of spectral values comprises a wavelength interval of at most 10 nm.

7. The method according to claim 1, wherein the vector of spectral values comprises: sampled spectral values; or spectral values averaged or summed over a wavelength interval.

8. The method according to claim 1, wherein the spectral values are intensities or a function of intensities of the captured reflected light.

9. The method according to claim 1, wherein the plurality of fiber material types comprises at least three fiber material types selected from the group consisting of: a cotton type, a wool type, a polyester type, an acrylic type, a viscose type, and a polyamide type.

10. The method according to claim 1, wherein the training of the deep neural network comprises an iterative optimization of the weights of the edges, preferably during a predefined number of iterations or until a predefined accuracy is reached.

11. The method according to claim 1, wherein the method comprises the steps of:
- obtaining for each of a white and a black calibration reference a calibration vector of spectral values; and
- normalizing a vector of spectral values of a sample with the calibration vectors of the black and white calibration references,
- wherein the normalized vector is input to the artificial neural network.

12. The method of claim 1, further comprising one or more of the following steps using a sorting apparatus, based on the output of the artificial neural network for each of a plurality of textile samples:
- sorting the textile samples;
- performing production quality control of the textile samples; and
- inspecting the accuracy of composition labels of the textile samples.

13. The method of claim 12, wherein the sorting apparatus further comprises multiple spatially separated output locations, wherein the method further comprises the steps of:
- determining an output location based on the output of the artificial neural network, wherein each determined output location is one of the multiple spatially separated output locations, each corresponding to a different composition category; and
- transporting the textile samples to the determined output location.

14. The method of claim 1, further comprising sequentially moving a plurality of textile samples relative to the test point via the transporting means; and acquiring and analyzing a spectrum for the plurality of textile samples at a rate faster than the rate of moving said textile samples relative to the test point.

15. The method of claim 14, further comprising determining a single vector of spectral values per textile sample;
- acquiring and analyzing a spectrum at a rate of from at most 20 milliseconds (msec) per textile sample to at most 50 msec per textile sample; and/or
- moving each textile sample relative to the test point at a rate of from at least 0.2 textile sample per second (textile sample/s) to at least 1 textile sample/s.

16. An apparatus for determining a fiber composition of a textile sample, comprising:
- a means for transporting the textile sample, the means for transporting the textile sample capable of moving the textile sample relative to a test point;
- a light source configured for irradiating the textile sample with near infrared light at the test point while the textile sample is moving relative to the test point via the means for transporting the textile sample;
- a capturing element configured for capturing reflected near infrared light from the textile sample at the test point while the textile sample is moving relative to the test point via the means for transporting the textile sample;
- a spectrometer configured for determining a vector of spectral values based on the captured light;
- a computer system, comprising at least one processor, configured for:
  - obtaining the vector from the spectrometer,
  - inputting the vector to an artificial neural network comprising nodes and edges, wherein each edge comprises a weight, and
  - obtaining output from the artificial neural network,
  - wherein the artificial neural network is a deep neural network comprising a sequence of layers of nodes, wherein the sequence comprises an input layer, a least two intermediate layers and an output layer, wherein nodes of successive layers of the sequence are interconnected via weighted edges, wherein the deep neural network is a feedforward neural network which is configured for data flow from the input layer to the output layer without looping back, wherein the output from the artificial neural network comprises for each of a plurality of fiber material types a numerical relative composition amount,
- preferably wherein the apparatus comprises a sensor head and a fiber optic cable in between the sensor head and the spectrometer, preferably wherein the sensor head comprises the light source and the capturing element, preferably wherein the spectrometer comprises a dispersing element and a detector,
- preferably wherein the apparatus comprises a conveyor belt for transporting the textile sample.

17. The apparatus of claim 16, wherein the transporting means is configured to sequentially move a plurality of textile samples relative to the test point; wherein the apparatus is configured to acquire and analyze a spectrum for the plurality of textile samples at a rate faster than the rate to move said textile samples relative to the test point.

18. The apparatus of claim 17, wherein the apparatus is configured to determine a single vector of spectral values per textile sample;
- wherein the apparatus is configured to acquire and analyze a spectrum at a rate of from at most 20 milliseconds (msec) per textile sample to at most 50 msec per textile sample; and/or
- wherein the apparatus is configured to move a textile sample relative to the test point at a rate of from at least 0.2 textile sample per second (textile sample/s) to at least 1 textile sample/s.

19. The apparatus of claim 18, further comprising multiple spatially separated output locations, and capable of:
- determining an output location based on the output of the artificial neural network, wherein each determined output location is one of the multiple spatially separated output locations, each corresponding to a different composition category; and
- transporting the textile samples to the determined output location.

20. The apparatus of claim 17, further comprising a sorting apparatus capable of one or more of the following, based on the output of the artificial neural network for each of a plurality of textile samples:
- sorting the textile samples;
- performing production quality control of the textile samples; and
- inspecting the accuracy of composition labels of the textile samples.

* * * * *